(12) United States Patent
Rayek et al.

(10) Patent No.: US 9,861,513 B2
(45) Date of Patent: Jan. 9, 2018

(54) SYSTEM AND METHOD FOR TREATING OBSTRUCTIVE SLEEP APNEA AND CORRECTING MALOCCLUSION SIMULTANEOUSLY

(71) Applicants: Riaz Rayek, Chantilly, VA (US); Jeffrey Tomcsik, Avenue, MD (US)

(72) Inventors: Riaz Rayek, Chantilly, VA (US); Jeffrey Tomcsik, Avenue, MD (US)

( * ) Notice: Subject to any disclaimer, the term of this patent is extended or adjusted under 35 U.S.C. 154(b) by 0 days.

(21) Appl. No.: 14/979,110

(22) Filed: Dec. 22, 2015

(65) Prior Publication Data
US 2016/0228286 A1 Aug. 11, 2016

Related U.S. Application Data

(60) Provisional application No. 62/095,358, filed on Dec. 22, 2014.

(51) Int. Cl.
*A61C 3/00* (2006.01)
*A61F 5/56* (2006.01)
*A61C 7/08* (2006.01)
*A61C 7/36* (2006.01)

(52) U.S. Cl.
CPC ............... *A61F 5/566* (2013.01); *A61C 7/08* (2013.01); *A61C 7/36* (2013.01)

(58) Field of Classification Search
CPC ............... A61F 5/566; A61C 7/08; A61C 7/36
USPC ................................................................. 433/6
See application file for complete search history.

(56) References Cited

U.S. PATENT DOCUMENTS

| 6,604,527 B1 * | 8/2003 | Palmisano | A61C 7/08 128/848 |
| 6,705,863 B2 * | 3/2004 | Phan | A61C 7/00 433/24 |

* cited by examiner

*Primary Examiner* — Yogesh Patel
(74) *Attorney, Agent, or Firm* — McKinney & Associates, LLC.; J. Andrew McKinney, Jr.

(57) ABSTRACT

A system and method for simultaneously (i) treating a patient's malocclusion by repositioning teeth from an initial tooth arrangement to a final tooth arrangement and (ii) treating Obstructive Sleep Apnea ("OSA") by forcing the mandible forward comprises a plurality of (e.g., 10-30) sets of individual appliances. The appliances are configured to be placed successively on the patient's upper and lower dental arches and to incrementally reposition the teeth and forcing the jaw forward, during sleep. The system of appliances is preferably configured at the outset of treatment so that the patient may progress through treatment without the need to have the treating professional perform each successive step in the procedure.

3 Claims, 3 Drawing Sheets

SYSTEM AND METHOD FOR TREATING OBSTRUCTIVE SLEEP APNEA AND CORRECTING MALOCCLUSION SIMULTANEOUSLY

PRIORITY CLAIM AND REFERENCE TO RELATED APPLICATION

This application claims priority to related and commonly owned U.S. provisional patent application No. 62/095,358, filed Dec. 22, 2014 and entitled System and Method for Treating Obstructive Sleep Apnea and Correcting Malocclusion Simultaneously, the entire disclosure of which is incorporated herein by reference.

BACKGROUND OF THE INVENTION

Field of the Invention

The present invention relates to Dental Appliances methods for treating Obstructive Sleep Apnea and malocclusion correction.

Discussion of the Prior Art

Individuals with Obstructive Sleep Apnea ("OSA") may have small, retruded chins and crowded lower teeth that cause the tongue to be pushed back against the airway, causing constriction of the airway, one of the primary causes of OSA. The obstruction in OSA is, more specifically, partial or complete obstruction of the upper airway during sleep. Sleep apnea causes drops in the blood oxygenation level and often adversely affects the heart by increasing blood pressure and pulse rate. Many aspects of a person's quality of life (e.g., physical and emotional health) are affected by OSA.

A typical approach for treating OSA is two-pronged, first, the patient is treated with traditional orthodontic appliances (e.g., braces) to expand the lower teeth at least partially and, second, the patient is fitted with a Mandibular Advancement Splint (MAS) appliance to move the lower jaw forward at night to lessen the patient's obstruction.

This two pronged approach is intended to lessen the severity of and treat the symptoms of OSA. An example of a Mandibular Advancement Splint ("MAS") device is found in U.S. Pat. No. 6,604,527, which is incorporated by reference for the sole purpose of providing technical and anatomical nomenclature.

In the OSA patient, sagittal mandibular or lower jaw movement occurs within a range limited by the border movements, broadly characterized by the most protruded path of opening and closure, the maximal open position of the mandible, the occlusal positions and the most retruded path of closure. In this sense, a reference herein to mandibular advancement represents locating the mandible so that it functions in the protruded range from the reflex or habital path of closure (occurring between the intercuspal occlusal position and the maximum open position) to the protrusive border path. Treatments using the MAS dental appliance (e.g., 90, as shown in FIG. 1B) push the lower jaw forward, and this treatment essentially involves wearing an appliance with upper and lower segments that engage each other (e.g., upper and lower flanges 92, 94) when the mouth is closed and the lower jaw is pushed forward, opening the airway.

Another treatment for obstructive sleep apnea involves wearing and sleeping with a Continuous Positive Airway Pressure (CPAP) mask, which pushes pressurized air into the lungs to get past the obstruction. CPAP is a well-known therapy for treating sleep apnea. OSA patients wear a CPAP face or nasal mask during sleep. The mask, connected to a pump, provides a positive flow of air into the nasal passages in order to keep the airway open. The CPAP form of treatment is cumbersome, difficult, uncomfortable and disruptive for the bed partners.

Malocclusion is the misalignment of teeth and/or an incorrect relation between the teeth of the upper and lower dental arches, giving rise to faulty contact between upper and lower teeth. Sometimes skeletal disharmony of the face, and in particular an incorrect relationship between the maxilla and mandible, is a contributing factor or even the root cause of malocclusion. The MAS device and method for mandibular advancement described in U.S. Pat. No. 6,604,527 is not configured to correct malocclusion, which is why prior art methods may require simultaneous use of braces.

For patients who have no issues with OSA, orthodontic treatment for malocclusion can be addressed using traditional braces or "clear aligner" treatments such as those sold under the brand name Invisalign® by Align Technologies, Inc. Invisalign® appliances are typically provided in pairs (for upper and lower arches, e.g., 80, as shown in FIG. 1A) each configured as a thin concave trough of material that forms a receiving cavity geometry generally conforming to a patient's teeth but slightly out of alignment with the initial tooth configuration.

Clear aligner appliances are made using polymers such as thermoplastic polyurethane. Polymers may deform over time and use due to external and internal forces. Deformation causing external forces may include flexion from repeated insertions and removals and deformation from biting or wearing the aligners. An internal deforming force may include material stress relaxation. The deformation may reduce tooth moving forces, thereby reducing the usefulness of the dental appliance. Once the usefulness of the aligner dental appliance is reduced, the dental appliance is typically discarded, and either a replacement dental appliance is made or the next dental appliance in the treatment series is used.

Clear aligners are like retainers (or trays) that move teeth over a period of time to correct misalignments, such as crowding. A series of aligners are made to treat each specific case, ranging from 10-30 aligners for an average patient. Patients typically wear a new set of aligners (upper and lower) every two weeks for a period of time as needed to make the alignment correction for the teeth.

The treatment for malocclusion and the treatment for OSA are completely separate and distinct modalities. Patients are treated orthodontically to expand the lower arch by correcting crowding (permanently) and a completely separate MSA appliance (e.g., 90, as shown in FIG. 1B) is also fitted to move their jaw (temporarily, while they sleep) to help with their breathing.

These two treatments (wearing braces and wearing an MSA splint) are problematic for the patient, since wearing braces (or clear aligners) makes wearing an MSA splint appliance awkward for some and impossible for others. There is a need, therefore, for a convenient, flexible, effective and unobtrusive system and method for treating OSA while simultaneously correcting malocclusion which overcomes these problems.

OBJECTS AND SUMMARY OF THE INVENTION

Accordingly, it is an object of the present invention to overcome the above mentioned difficulties by providing an improved system and method for treating obstructive sleep apnea ("OSA") and correcting malocclusion simultaneously, without requiring the patient to simultaneously wear orthodontic braces or clear aligners with an incompatible, awkward Mandibular Advancement Splint ("MAS") appliance.

In accordance with the present invention, a method for treating obstructive sleep apnea and correcting malocclusion simultaneously includes using a series of combined use Mandibular Splint ("MS") aligner appliances in matching pairs having a first, upper MS-aligner and second lower MS-aligner; where the first MS-aligner is shaped to engage a patient's upper arch and the second aligner is shaped to engage the patent's lower arch, and where series of first and second MS-aligners, when used in sequence, are configured to correct a specific malocclusion for the patient. The upper MS-aligners all carry or incorporate at least one MS ridge member on each side, and the lower aligners all carry a MS fin member on each side. When the upper and lower MS aligners are fitted into the patient's mouth, each upper MS aligner ridge engages a corresponding low MS aligner's fin and prevents that cooperating fin from moving backwards, thereby preventing the lower arch (and mandible) of the patient from moving backwards, thus treating the patient's OSA symptoms.

Another object of the system and method of the present invention for treating obstructive sleep apnea and correcting malocclusion simultaneously is to provide a cost-beneficial solution for manufacturers and patients by providing an attachment to the upper and lower MS aligners to allow for the use of the same MS ridge and MS fin to be attached to each upper & lower set of aligners used by the patient during their treatment.

Another object of the system and method of the present invention for treating obstructive sleep apnea and correcting malocclusion simultaneously is to reduce the time needed for treatment. In accordance with the method of the present invention, treatment for both obstructive sleep apnea and correction of the malocclusion is simultaneously accomplished by the patient's insertion of the upper and lower MS aligners, thereby reducing the total time necessary, because treatment for the OSA does not have to be given before or after orthodontic treatment of a malocclusion.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

DESCRIPTION OF THE PREFERRED EMBODIMENT

Referring now to FIGS. 2-7, the present invention comprises a system and method for treating obstructive sleep apnea ("OSA") and correcting malocclusion simultaneously.

Figure 1A:
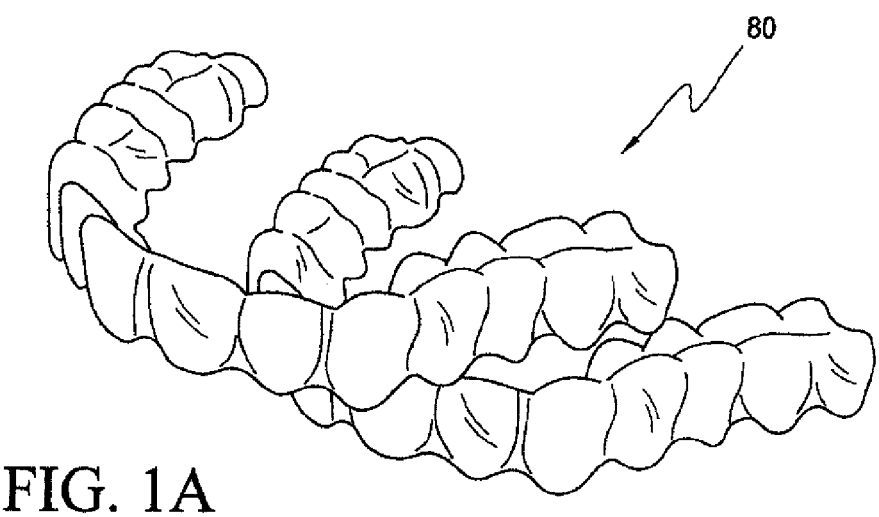
FIG. 1A illustrates a typical prior art Clear Aligner set, for purposes of establishing reference nomenclature.
Figure 1B:
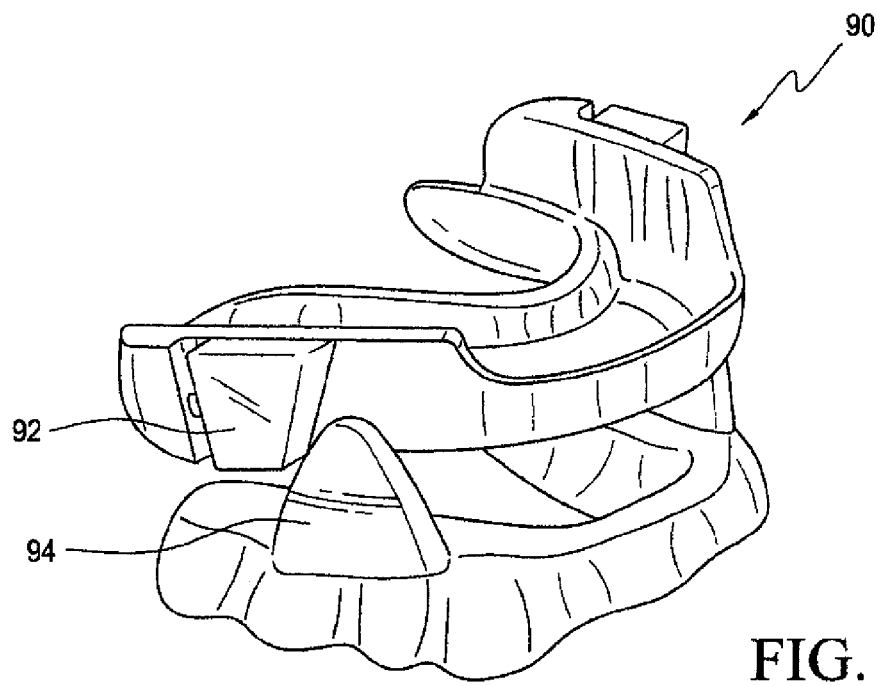
FIG. 1B illustrates a typical prior art mandibular advancement splint ("MAS") appliance, for purposes of establishing reference nomenclature.
Figure 2:
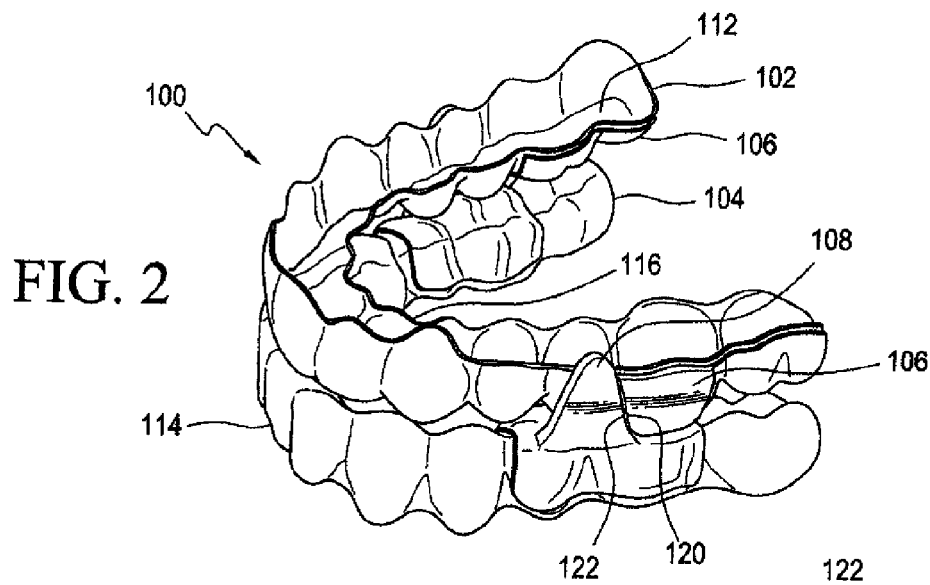
FIG. 2 illustrates a perspective view of Mandibular Splint ("MS") aligner appliance set illustrating part of the system and method for treating obstructive sleep apnea ("OSA") and correcting malocclusion simultaneously, in accordance with the present invention.

Referring first to FIG. 2, Mandibular Splint ("MS") Aligner appliance 100 comprises first, upper MS-Aligner 102 and second lower MS-Aligner 104 which are configured as a set for use by a patient who will be fitted for and wear a sequence of between 10 and 30 sets of Mandibular Splint ("MS") aligner appliances. The complete array of (e.g., 30) sets of Mandibular Splint ("MS") aligner appliances, when used in sequence, are adapted to (a) reposition a specific patient's teeth (not shown) from an initial tooth arrangement to a final tooth arrangement over a period of time and correct malocclusion while simultaneously (b) treating the patient's OSA by pushing the lower jaw forward by having the Fin members 108 and Ridge members 106 engage each other (when the patient's mouth is substantially closed, during sleep) to bias or force the patient's lower jaw forward, thereby establishing and maintaining an un-occluded or open airway during sleep.

In accordance with the method of the present invention, obstructive sleep apnea and malocclusion are treated simultaneously using a series of (e.g. 10-30 sets of) combined use Mandibular Splint ("MS") aligner appliances 100 in matching pairs having a first, upper MS-aligner 102 and second, lower MS-aligner 104. The first, upper MS-aligner 102 is shaped to engage a patient's upper arch and the second, lower aligner 104 is shaped to engage the patent's lower arch. The series of first and second MS-aligners, when used in sequence, are configured to correct a specific malocclusion for the patient. The upper MS-aligners 102 (e.g., as illustrated in FIG. 2) all carry or incorporate at least one MS Ridge member 106 defining a fin engagement surface 120 on a selected side (e.g., left or right, and preferably one on each side, as shown in FIG. 2). The lower aligners 104 all carry at least one MS Fin member 108 on a selected side (e.g., left or right, and preferably one on each side, as shown in FIG. 2). When the upper and lower MS aligners 102, 104 are fitted into the patient's mouth, each upper MS aligner ridge engagement surface 120 engages and bears against a corresponding lower MS aligner's fin 108 and prevents that cooperating fin from moving backwards or proximally, thereby preventing the lower arch (and mandible) of the patient from moving backwards or proximally, thus treating the patient's OSA symptoms.

FIGS. 2-7 illustrate two exemplary embodiments 100, 200 of the system and method for treating apnea and malocclusion of the present invention. More specifically, the system of the present invention comprises a series of dental appliances for simultaneously (i) treating a patient's malocclusion by repositioning teeth from an initial tooth arrangement to a final tooth arrangement and (ii) treating OSA by biasing or forcing the patient's mandible forward. The series of (e.g., 10-30) sets of individual appliances are configured to be placed successively on the patient's upper and lower dental arches to incrementally reposition the teeth from an initial tooth arrangement, through a plurality of intermediate tooth arrangements, and to a final tooth arrangement. The system of appliances (e.g., 100, 200) is usually configured at the outset of treatment so that the patient may progress through treatment without the need to have the treating professional perform each successive step in the procedure.

As shown in FIG. 2, an exemplary Mandibular Splint ("MS") aligner appliance set 100 includes an upper arch aligner 102 and lower arch aligner 104. Each arch aligner (102, 104) comprises a shell including a concave trough conforming closely to a specific patient's plurality of teeth and snugly engages the patent's teeth when placed over the teeth. Each concave trough is preferably made from a shape memory polymer material that is transitionable to the approximate original shape from the relaxed shape upon application of an external stimulus. The original shape is configured to apply a desired corrective force on selected teeth in the patient's arch when the trough conforms (upon placement on the teeth). Each AS aligner shell member has an inner cavity 112, a front, outer or distal edge 114, and a rear, inner or proximal distal edge 116. The inner cavity is shaped to receive and resiliently reposition the patient's teeth from one tooth arrangement to a successive tooth arrangement, as is customary for standard orthodontic clear aligner appliances. As noted above, clear aligner orthodontic treatments are sold under the brand name Invisalign® by Align Technologies, Inc. The Invisalign® clear alignment systems and methods are described and illustrated in several patents including U.S. Pat. No. 6,471,511, U.S. Pat. No. 6,217,325, U.S. Pat. No. 5,975,893, U.S. Pat. No. 6,705,863, U.S. Pat. No. 6,722,880, U.S. Pat. No. 7,125,248, U.S. Pat. No. 7,134,874, and U.S. Pat. No. 7,578,674, which are incorporated herein by reference for the sole purpose of providing technical and orthodontic nomenclature.

The upper arch aligner 102 of the present invention preferably comprises left side and right side (or first and second opposing) laterally projecting bosses or ridge members 106 and is firmly received and fitted over the upper teeth. The laterally projecting ridge features 106 are positioned upon and carried by an external surface of the aligner upper shell member 102 close to the shell's exterior surface segment configured for receiving the posterior (i.e., back") teeth or larger molars.

The lower arch aligner shell member 104 preferably comprises left side and right side (or first and second opposing) upwardly projecting substantially triangular, planar fin members 108 and is firmly received and fitted over the lower teeth. The fins 108 are positioned on or carried by lower shell 104 in an orientation configured to cooperate with and engage ridge features 106 on the upper aligner 102 and so are preferably positioned on an external surface of aligner lower shell member 104 beside and close to the aligner segment configured to receive the posterior teeth or larger molars, but slightly forward or proximal of the corresponding attachment point for the corresponding upper shell's ridge features, as best seen in FIG. 2, which shows the aligners oriented as they would be when worn by a patient whose mouth is closed, during sleep.

Figure 3:
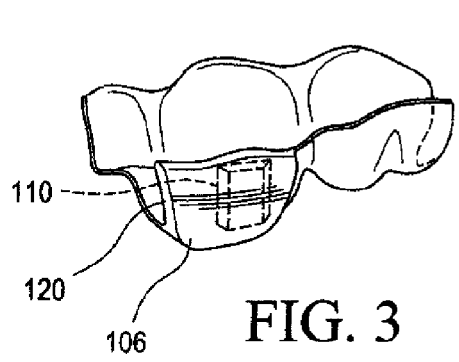
FIG. 3 illustrates, in perspective, a detailed segment view of an optional MS ridge member component adapted for removable attachment to and use with Mandibular Splint ("MS") aligner appliance of FIG. 2, showing a detailed view of the left side ridge's fin engagement surface, in accordance with the present invention.
Figure 5:
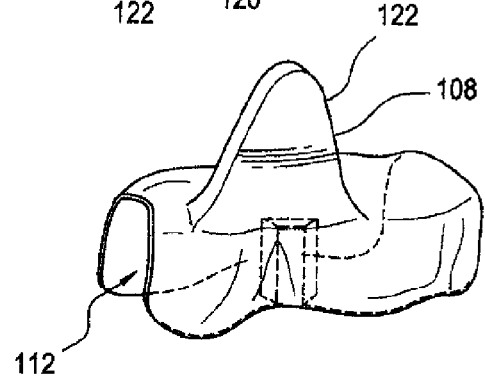
FIG. 5 illustrates, in perspective, a detailed segment view of an optional MS fin member component adapted for removable attachment to and use with Mandibular Splint ("MS") aligner appliance of FIG. 2, noting the left side fin's ridge engagement surface, in accordance with the present invention.
Figure 4:
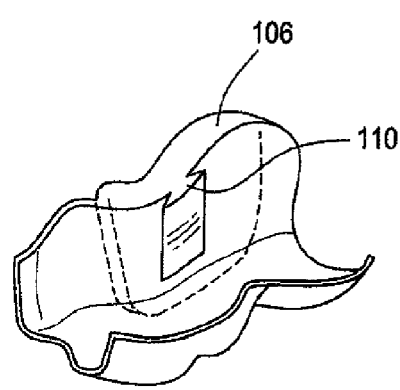
FIG. 4 illustrates, in perspective, a detailed segment view of an optional MS ridge member component adapted for removable attachment to and use with Mandibular Splint ("MS") aligner appliance of FIG. 2, showing a detailed view of the right side ridge's dove-tail shaped aligner-engagement tab, in accordance with the present invention.
Figure 6:
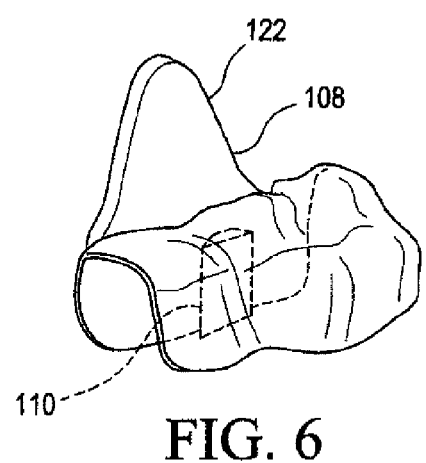
FIG. 6 illustrates, in perspective, a detailed segment view of an optional MS fin member component adapted for removable attachment to and use with Mandibular Splint ("MS") aligner appliance of FIG. 2, showing (in hidden lines) a detailed view of the right side fin's dove-tail shaped aligner-engagement tab, in accordance with the present invention.

FIG. 3 illustrates, in perspective, a detailed segment view of an optional MS ridge member component adapted for removable attachment to and use with Mandibular Splint ("MS") aligner appliance of FIG. 2, showing a detailed view of the left side ridge's fin engagement surface 120, and FIG. 4 shows the corresponding right side ridge member's upward facing conformal cavity with an inwardly projecting dove-tail shaped aligner-engagement tab 110, in accordance with the present invention. Similarly, FIG. 5 illustrates, in perspective, a detailed segment view of an optional MS fin member component adapted for removable attachment to and use with Mandibular Splint ("MS") aligner appliance of FIG. 2, noting the left side fin's ridge engagement surface 122, and FIG. 6 shows the corresponding right side fin's dove-tail shaped aligner-engagement feature or tab 110, in hidden lines.

The forward, distal or leading edge 120 of each laterally projecting ridge 106 forms an angled fin engagement surface 120, sloping proximally from top to bottom at a selected engagement angle of between 15 and 40 degrees from vertical (in the illustrated example, approximately 30 degrees). The rearward, proximal or trailing edge 122 of each fin 108 defines a cooperating angled engagement surface (also sloping proximally from top to bottom at a selected engagement angle of between 15 and 40 degrees from vertical, and in the illustrated example, approximately 30 degrees), and each fin's ridge engagement surface 122 compliments, abuts and bears against the corresponding distal engagement surface 120 defining the leading edges of the corresponding ridge 106, when the patient's mouth is closed, as during sleep.

As noted above, when correcting malocclusion, it takes more than one set or pair of arch aligners (e.g., 102, 104) to make the correction. Over time, new pairs of aligners (e.g., upper arch aligner 102 and lower arch aligner 104), are needed to make a new incremental adjustment to the teeth to correct the malocclusion. In the system of the present invention, each set of aligners may either be configured with permanent, (molded in situ) integral fins and ridges (thereby providing nighttime-only aligners), or the fins and ridges (e.g., 106, 108, 206, 208) may be removably installed upon each arch aligner in the series of sets, so that the upper and lower aligners (e.g., 202, 204) may be worn during the day without fins and ridges.

Thus, one embodiment of the present system 100 has the ridges 106 and fins 108 affixed permanently to or molded in situ upon and integral with each pair of arch aligners (102, 104). In this embodiment of the method of the present invention, if a user requires twenty pairs of arch aligners, then the attending professional will arrange for fabrication of twenty nighttime arch aligner, sets, each set with ridges 106 and fins 108, before the aligners sets are given to the patient. Therefore there will be twenty sets of aligners 104, 106, each configured with ridges and fins positioned to treat that patient's malocclusion and OSA simultaneously during a given evening's sleep. In this embodiment of the system (e.g., 100) and method of the present invention, the patient is preferably also fitted for and wears a corresponding set of conventional clear aligner appliances (e.g., 80) for use during the day.

In an alternative embodiment of the system of the present invention 200, the patient uses one set of ridges 206 and fins 208 for all of the pairs of arch aligners (202, 204) for the correction of malocclusion, and wears the detachable MS fin and ridge receiving arch aligners 202, 204, day and night, thus saving the expense associated with a separate set of daytime aligners 80. In this alternative embodiment, if a patient requires twenty pairs of arch aligners, there will only be one pair (left side and right side) of ridge members 206 and a corresponding pair of fin members 208 configured for use used for all twenty pairs of arch aligners. The ridges 206 and fins 208 are affixed to each pair of arch aligners (202, 204) by use of a dove-tail shaped aligner-engagement feature or tab 110 which engages a corresponding dove-tail shaped engagement receiving feature or slot 211 defined in a side surface of the corresponding aligner shell (e.g., 202, 204, as illustrated in FIG. 7).

In the method of the present invention, releasably detachable left and right side MS fin members 208, and releasably detachable left and right side MS ridge members 206 provide the same functional and therapeutic benefits as the MS ridges 106 and MS fins 108 used in Mandibular Splint ("MS") aligner appliance 100, but the ridge members and fin members may be applied to selected aligner members or shells 202, 204 as those aligner shells are used, in sequence, allowing the patient or professional to decide when to use the MS fin members 208 and MS ridge members 206 and saving money, since the MS fin members and MS ridge members need not be discarded when used aligner shells are discarded and the removable MS member compatible arch aligners 202, 204 may be worn day or night.

Figure 7:
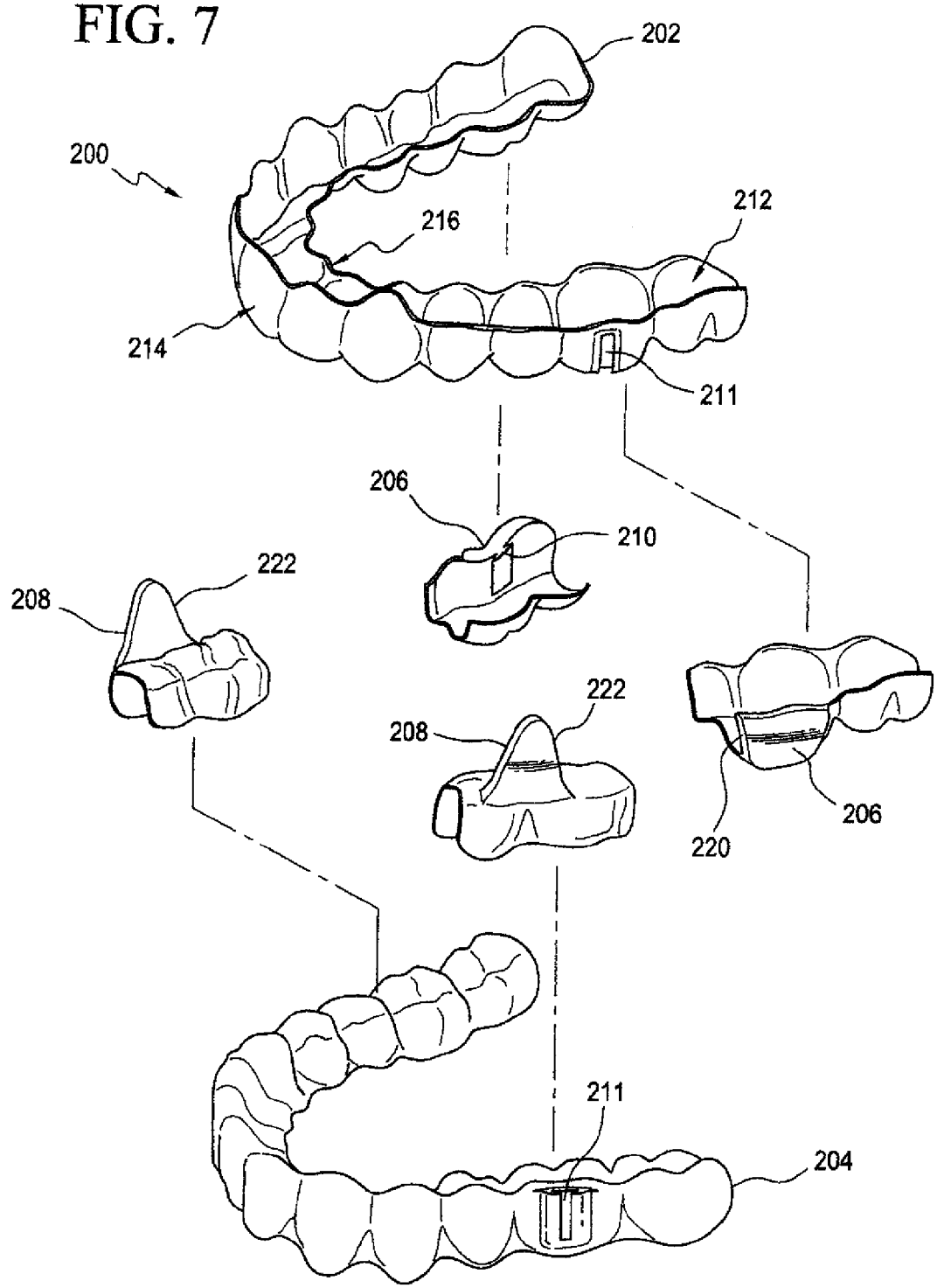
FIG. 7 illustrates, in perspective, an exploded view of an alternative embodiment including a six-part Mandibular Splint ("MS") aligner appliance set including an MS upper aligner and a MS lower aligner configured to releasably receive and carry the MS fin and ridge components of FIGS. 2-6, in accordance with the system and method of the present invention.

FIG. 7 illustrates the embodiment of the system 200 and method for treating obstructive sleep apnea and correcting malocclusion simultaneously, with selectively attachable and detachable MS fin members 208 and selectively attachable and detachable MD ridge members 206. Arch aligners (202, 204) have lateral sidewalls with the releasable attachment feature or dove-tail slot or groove 211 defined therein to firmly receive the corresponding inwardly projecting attachment tab, protuberance or feature 210 by sliding the tab for either ridge 206 or fin 208 into its respective groove 211 where it is preferably received and retained by friction fit so that there is no interference in the upper and lower alignment or "bite" experienced by the patient when wearing the aligners 202, 204. The leading edge 220 defined on the external surfaces of each ridge member 206 forms an angled or inclined engagement surface, as described above for ridge 106. The trailing edge of each substantially triangular fin member 208 forms a cooperating angled engagement surface 222 complementing the engagement surfaces of the leading edges 220 of ridges 206.

It will be appreciated by those of skill in the art that the system (e.g., 100, 200) for simultaneously treating obstructive sleep apnea and correcting malocclusion simultaneously comprises a number of features which, together, provide a surprisingly effective way for patients to overcome the problems with the prior art: namely (a) use of a first (102, 202) and second (104, 204) aligner, where the first aligner (102, 202) is shaped to engage the upper arch of a patient and the second aligner (104, 204) is shaped to engage the lower arch of the patient and the first and second aligners are configured to correct malocclusion of the patient;

(b) an MS ridge (106, 206), where the ridge is connected to the first aligner (102, 202); and (c) an MS fin (108, 208), where the fin is connected to the second aligner (104, 204); where the ridge (106, 206) engages with the fin (108, 208) and prevents the fin from moving backwards thereby preventing the lower arch or mandible of a patient from moving backwards or proximally.

The system (e.g., 100, 200) for treating obstructive sleep apnea and correcting malocclusion simultaneously thus includes the following features:

(a) a first or upper arch aligner (102, 202) and a second or lower arch aligner (104, 204), where the first aligner (102, 202) is shaped to engage the upper arch of a user and the second aligner (104, 204) is shaped to engage the lower arch of the user, and where the first (102, 202) and second aligners (104, 204) are configured with the assistance and guidance of a treating professional to correct a specific malocclusion of the patient or user;

(b) a laterally projecting MS ridge feature (106, 206), where the ridge is connected to the first aligner; and (c) an upwardly projecting MS fin feature (108, 208), where the fin is connected to the second aligner; where, when the upper and lower arch aligners are worn by the patient and the patient's mouth is closed (as during sleep) the MS ridge (106, 206) engages with the MS fin (108, 208) and prevents the MS fin (108, 208) from moving backwards thereby preventing the patient's lower arch from moving backwards or proximally. Optionally, either the ridge member (106, 206) is releasably connected to the first aligner (102, 202) by a removable attachment (110, 210), or the fin member (108, 208) is connected to the second aligner (104, 204) by an attachment (110, 210).

Broadly speaking, the system for treating obstructive sleep apnea and correcting malocclusion simultaneously of the present invention includes the following features:

(a) a first (102, 202) and second (104, 204) aligner, where the first aligner (102, 202) is shaped to engage the upper arch of a user and the second aligner (104, 204) is shaped to engage the lower arch of the user and the first (102, 202) and second (104, 204) aligners are configured to correct malocclusion and obstructive sleep apnea of the user;

(b) a ridge (106, 206), where the ridge is adapted onto the first aligner directly;

(c) a fin (108, 208), where the fin is adapted onto the second aligner directly; and where the ridge (106, 206) engages with the fin (108, 208) and prevents the fin (108, 208) from moving backwards thereby preventing the lower arch of a user from moving backwards.

An orthodontic device for treating obstructive sleep apnea and correcting malocclusion simultaneously comprises:

(a) a first (102, 202) and second (104, 204) aligner, where the first aligner (102, 202) is shaped to engage the upper arch of a user and the second aligner (104, 204) is shaped to engage the lower arch of the user and the first (102, 202) and second (104, 204) aligners are configured to correct malocclusion of the user;

(b) a ridge (106, 206), where the ridge is connected to the first aligner; and (c) a fin (108, 208), where the fin is connected to the second aligner;

where the ridge engages with the fin and prevents the fin from moving backwards thereby preventing the lower arch of a user from moving backwards.

A system for treating obstructive sleep apnea and correcting malocclusion simultaneously comprises:

(a) a first appliance (202, 204) having a geometry selected to reposition the teeth from the initial tooth arrangement to a first intermediate arrangement;

(b) one or more intermediate appliances (202, 204) having different teeth-receiving cavity geometries based on successive intermediate tooth arrangements, the geometries selected to progressively reposition the teeth from the first intermediate arrangement to successive intermediate arrangements; and (c) a final appliance (202, 204) having a geometry selected to progressively reposition the teeth from a last intermediate arrangement to the final tooth arrangement, where the appliances comprise polymeric shells having cavities 212 and where the teeth-receiving cavities of successive shells have different geometries shaped to receive and resiliently reposition teeth from one arrangement to a successive arrangement, where at least one of the successive intermediate tooth arrangements is generated prior to generating a preceding successive intermediate tooth arrangement, (d) where the first, intermediate, and final appliances have
at least one lower component having an attachment structure 211 that is releasably attachable to at least a portion of the lower jaw and an engagement surface extending upwardly from the attachment structure 208; and
at least one upper component having an attachment structure 211 that is releasably attachable to at least a portion of the upper jaw and an engagement surface extending downwardly from the attachment structure 206; and
where, when the lower and upper engagement members are fitted to the jaws of a patient for use in sleep, the lower and upper engagement surfaces (206, 208) engage at a location lying in an area beside and close to the posterior teeth in a manner to cause advancement of the lower jaw from the reflex path of opening and maintain the engagement and advancement, while permitting sagittal movement, up to the normal range of jaw opening extending from an advanced occluding position by remaining fitted to the jaws of the patient when in use.

The method for treating obstructive sleep apnea and correcting malocclusion simultaneously using the systems (100, 200) described above includes the following method steps:

(a) providing a set of at least first and second dental incremental position adjustment appliances or shells (202, 204) having different successive teeth-receiving cavity geometries 212 to a treating professional;

(b) subsequent to the providing step, placing a first incremental position adjustment appliance from the set of appliances in a patient's mouth, where the first appliance has a geometry selected to reposition the teeth from the initial tooth arrangement to the first intermediate arrangement;

(c) fitting the dental incremental position adjustment appliances, having upper 206 and lower 208 components or shells, upon the upper and lower dental arches or upper and lower teeth of a patient;

(d) installing or mounting each of the upper shell MS components 206 and lower shell MS components 208 by attaching those MS components to the upper and lower shells at corresponding MS component mounting features 211 which are location in on the lateral sidewall surfaces of the shells 202, 204 an area beside and close to shall cavity segment configured to receive and snugly retain the patient's back or posterior teeth;

(e) forcing, biasing or urging (i.e., causing advancement of) the lower jaw from the reflex path of opening; and maintaining engagement and advancement, while permitting sagittal movement, up to the normal range of jaw opening extending from an advanced occluding position by the components remaining fitted to the jaws of the patient simultaneously;

(f) successively replacing one or more additional appliances (202, 204) from the set in the patient's mouth with the next incremental position adjustment appliance of the set, where the additional appliances have geometries selected to progressively reposition the teeth from the first intermediate arrangement to successive intermediate arrangements and having upper 206 and lower 208 components, to the jaws of a patient, the components engaging at a location in an area beside and close to the posterior teeth and causing advancement of the lower jaw from the reflex path of opening; and maintaining engagement and advancement, while permitting sagittal movement, up to the normal range of jaw opening extending from an advanced occluding position by the components remaining fitted to the jaws of the patient simultaneously; and (g) placing a final appliance into the patient's mouth, where the final appliance has a geometry selected to progressively reposition the teeth from a last intermediate arrangement to the final tooth arrangement, where the appliances comprise polymeric shells having cavities, and where the teeth-receiving cavities of successive shells have different geometries shaped to receive and resiliently reposition teeth form one arrangement to a successive arrangement and having upper 206 and lower 208 components, to the jaws of a patient, the components engaging at a location in an area beside and close to the posterior teeth and causing advancement of the lower jaw from the reflex path of opening; and maintaining engagement and advancement, while permitting sagittal movement, up to the normal range of jaw opening extending from an advanced occluding position by the components remaining fitted to the jaws of the patient simultaneously.

Having described preferred embodiments of a new and improved method, it is believed that other modifications, variations and changes will be suggested to those skilled in the art in view of the teachings set forth herein. It is therefore to be understood that all such variations, modifications and changes are believed to fall within the scope of the present invention as set forth in the appended claims.

We claim:

1. A method for treating obstructive sleep apnea and correcting malocclusion simultaneously comprising:

(a) providing a set with at least two dental incremental position adjustment appliances having different successive teeth-receiving cavity geometries to a treating professional, wherein each incremental position adjustment appliance comprises an upper aligner configured to receive and support a first releasably detachable mandibular splint member component and a lower aligner configured to receive and support a second releasably detachable mandibular splint member component;

(b) subsequent to the providing step, placing a first incremental position adjustment appliance from the set of appliances in a patient's mouth, wherein the first appliance has a geometry selected to reposition the teeth from an initial tooth arrangement to a first intermediate arrangement;

(c) installing, in said dental incremental position adjustment, appliance's upper aligner, the first releasably detachable mandibular splint member component and installing, in said incremental position adjustment appliance's lower aligner, the second releasably detachable mandibular splint member component, and fitting said incremental position adjustment appliance to the jaws of the patient such that the first and second mandibular splint components engage at a location in an area beside and close to the posterior teeth and thus bias or urge the lower jaw distally, causing advancement of the lower jaw from the reflex path of opening; and maintaining engagement and advancement, while permitting sagittal movement, up to the normal range of jaw opening extending from an advanced occluding position by said first and second mandibular splint components remaining fitted to the jaws of the patient simultaneously.

2. The method of claim 1, further comprising:

(d) successively replacing one or more additional appliances from the set in the patient's mouth with the next incremental position adjustment appliance of the set, wherein the additional appliances have geometries selected to progressively reposition the teeth from the first intermediate arrangement to successive intermediate arrangements and having first and second mandibular splint components, to the jaws of a patient, the first and second mandibular splint components engaging at a location in an area beside and close to the posterior teeth and causing advancement of the lower jaw from the reflex path of opening; and maintaining engagement and advancement, while permitting sagittal movement, up to the normal range of jaw opening extending from an advanced occluding position by said first and second mandibular splint components remaining fitted to the jaws of the patient simultaneously.

3. The method of claim 1, further comprising:

(e) placing a final appliance into the patient's mouth, wherein the final appliance has a geometry selected to progressively reposition the teeth from a last intermediate arrangement to the final tooth arrangement, wherein the appliances comprise polymeric shells having cavities, and wherein the teeth-receiving cavities of successive shells have different geometries shaped to receive and resiliently reposition teeth form one arrangement to a successive arrangement and having upper and lower components, to the jaws of a patient, and wherein said first and second mandibular splint components are installed to engage at a location in an area beside and close to the posterior teeth and causing advancement of the lower jaw from the reflex path of opening; and maintaining engagement and advancement, while permitting sagittal movement, up to the normal range of jaw opening extending from an advanced occluding position by said components remaining fitted to the jaws of the patient simultaneously.

* * * * *